United States Patent [19]

Vuligonda et al.

[11] Patent Number: 6,043,381

[45] Date of Patent: Mar. 28, 2000

[54] PROCESS FOR PREPARING SUBSTITUTED BENZO[1,2-G]-CHROM-3-ENE, BENZO[1,2-G]-THIOCHROM-3-ENE AND BENZO[1,2-G]-1,2-DIHYDROQUINOLINE DERIVATIVES

[75] Inventors: Vidyasagar Vuligonda, Irvine; Roshantha A. Chandraratna, Mission Viejo, both of Calif.

[73] Assignee: Allergan Sales, Inc., Irvine, Calif.

[21] Appl. No.: 09/307,062

[22] Filed: May 7, 1999

[51] Int. Cl.$^7$ .................................................. C07D 311/92
[52] U.S. Cl. .......................... 549/389; 549/60; 546/282.7; 548/202; 548/235; 548/311.4; 544/238; 544/333; 544/405
[58] Field of Search ............................ 549/359, 60, 389; 546/282.7; 544/238, 333, 405; 548/202, 235, 311.4

[56] References Cited

U.S. PATENT DOCUMENTS

| | | | |
|---|---|---|---|
| 5,523,457 | 6/1996 | Starrett, Jr. et al. | 560/24 |
| 5,559,248 | 9/1996 | Starrett, Jr. et al. | 549/79 |
| 5,648,514 | 7/1997 | Johnson et al. | 560/102 |
| 5,728,846 | 3/1998 | Vuligonda et al. | 549/16 |
| 5,877,207 | 3/1999 | Klein et al. | 514/456 |

FOREIGN PATENT DOCUMENTS

| | | | |
|---|---|---|---|
| 0661259 | 7/1995 | European Pat. Off. | C07C 233/81 |
| 94/14777 | 7/1994 | WIPO | C07D 231/54 |

OTHER PUBLICATIONS

Dawson and William H. Okamura, *Chemistry and Biology of Synthetic Retinoids*, published by CRC Press, Inc., 1990, pp. 334–335, 354 and 324–356.
Sundberg et al., J. Org. Chem. (1967) 32, p. 2938.
Murphy et al., J. Med. Chem. (1990) 33, p. 171.

*Primary Examiner*—Amelia Owens
*Attorney, Agent, or Firm*—Gabor L. Szekeres; Robert J. Baran; Martin A. Voet

[57] ABSTRACT

Compounds of Formula 1

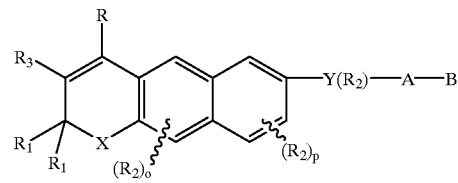

Formula 1 where the symbols have the meaning disclosed in the specification are prepared by reaction of a compound of Formula 2

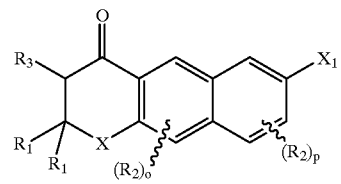

Formula 2 with an organometal reagent R—M to provide a compound of Formula 3

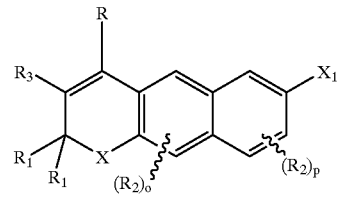

Formula 3 that is reacted with the reagent $X_3$—$Y(R_2)$—A—B in the presence of a catalyst to provide the compounds of Formula 1.

22 Claims, No Drawings

PROCESS FOR PREPARING SUBSTITUTED BENZO[1,2-G]-CHROM-3-ENE, BENZO[1,2-G]-THIOCHROM-3-ENE AND BENZO[1,2-G]-1,2-DIHYDROQUINOLINE DERIVATIVES

BACKGROUND OF THE INVENTION

1. Field of the Invention

The present invention relates to a synthetic process for preparing benzo[1,2-g]-chrom-3-ene, benzo[1,2-g]-thiochrom-3-ene and benzo[1,2-g]-1,2-dihydroquinoline derivatives which bind to retinoid receptors and have retinoid-like, retinoid antagonist or retinoid inverse agonist-like biological activity. More specifically, the present invention relates to a synthetic process for preparing certain benzo[1,2-g]-chrom-3-ene, benzo[1,2-g]-thiochrom-3-ene and benzo[1,2-g]-1,2-dihydroquinoline derivatives which are described in U.S. Pat. No. 5,728,846 and which bind to retinoid receptors and primarily have retinoid antagonist or retinoid inverse agonist-like biological activity.

2. Background Art

U.S. Pat. No. 5,728,846 discloses substituted benzo[1,2-g]-chrom-3-ene, benzo[1,2-g]-thiochrom-3-ene and benzo [1,2-g]-1,2-dihydroquinoline derivatives which bind to retinoid receptors and have retinoid-like, retinoid antagonist or retinoid inverse agonist-like biological activity. Other examples of compounds having retinoid-like biological activity and condensed tricyclic or dihydronaphthalene structure are found in the following U.S. and foreign patent disclosures: U.S. Pat. Nos. 5,523,457; 5,559,248; 5,648,514; 5,877,207, WO 94/14777 and EPO 0 661-259 A1.

The publication Dawson and William H. Okamura, *Chemistry and Biology of Synthetic Retinoids,* published by CRC Press Inc., 1990, pages 334–335, 354 and 324–356 is of special interest as an overview of the chemistry and biology of retinoid-like compounds.

Among the compounds disclosed in U.S. Pat. No. 5,728,846, benzo[1,2-g]-chrom-3-ene derivatives, and particularly 4-[2,2-dialkyl-4-(aryl, heteroaryl or alkyl)-6,7-benzochrom-3-en-7-yl]benzoic acids or benzoic acid esters are of particular interest primarily as retinoid antagonist and/or retinoid inverse agonist compounds. Whereas U.S. Pat. No. 5,728,846 discloses synthetic processes for the preparation of these compounds, the present invention describes a different and significantly improved synthetic process for the preparation of this class of compounds.

SUMMARY OF THE INVENTION

The present invention relates to the synthetic process for making compounds of Formula 1,

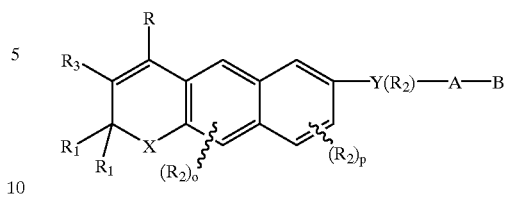

Formula 1 where X is O, S, NH or N-lower alkyl of 1 to 6 carbons;

R is alkyl of 1 to 10 carbons, alkenyl of 1 to 10 carbons and of 1 to 3 double bonds, alkynyl of 1 to 10 carbons and of 1 to 3 triple bonds, $(R_4)_s$-aryl or $(R_4)_s$-heteroaryl where heteroaryl is selected from the group consisting of pyridyl, thienyl, furyl, pyridazinyl, pyrimidinyl, pyrazinyl, thiazolyl, oxazolyl, imidazolyl and pyrrazolyl;

$R_1$ is lower alkyl of 1 to 6 carbons;

$R_2$ and $R_4$ independently are alkyl of 1 to 6 carbons, F, Cl, Br, I, $NO_2$, $N_3$, $(CH_2)_pCOOH$, $(CH_2)_pCOOR_1$;

o, p and s are integers each independently having the value of 0 to 2;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or Y is —$(CR_3=CR_3)_2$—;

$R_3$ is H or lower alkyl of 1 to 6 carbons;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, with the proviso that when Y is $(CR_3=CR_3)_2$— then A is $(CH_2)_q$ and q is 0;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or $Si(C_{1-6}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

REACTION SCHEME 1

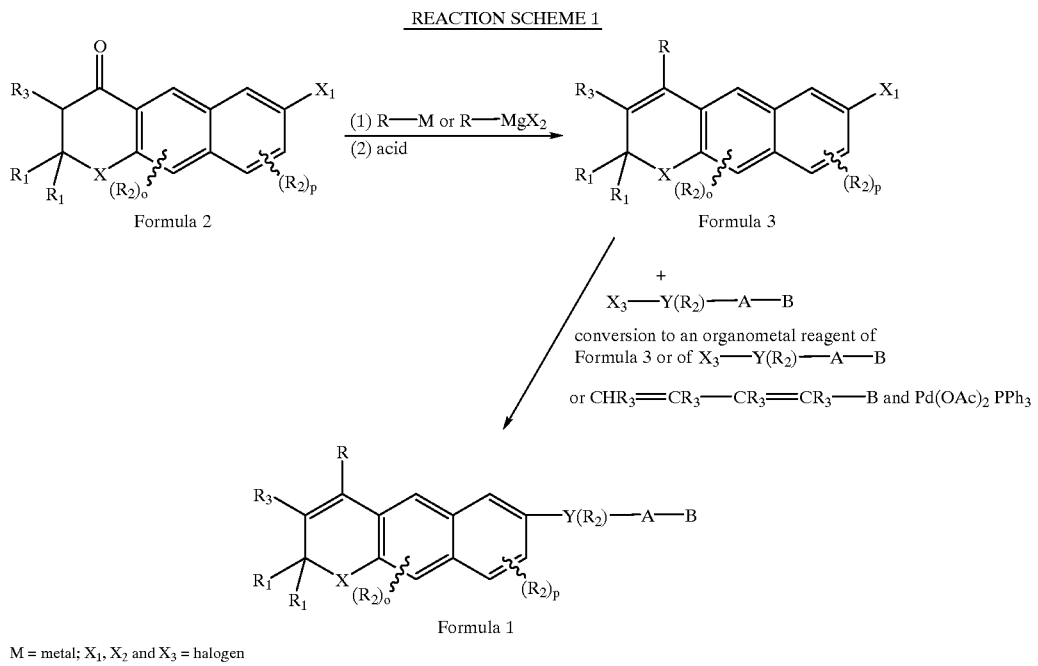

M = metal; $X_1, X_2$ and $X_3$ = halogen

The inventive process comprises the steps shown in Reaction Scheme 1 where a condensed tricyclic ketone compound of Formula 2 is reacted with an organometal reagent under conditions in which the organometal reagent selectively reacts with the endocyclic ketone of the compound of Formula 2, in preference over reacting with the halogen substituent $X_1$. The symbols X, $R_1$, $R_2$ and R are defined in Reaction Scheme 1 as in connection with Formula 1. The resulting intermediate tertiary alcohol (not shown in the scheme) is dehydrated by treatment with acid to provide a benzo[1,2-g]-chrom-3-ene, benzo[1,2-g]-thiochrom-3-ene and benzo[1,2-g]-1,2-dihydroquinoline derivative of Formula 3 that still has the halogen substituent $X_1$ in the 7 position of the benzo[1,2-g]-chrom-3-ene, benzo[1,2-g]-thiochrom-3-ene and benzo[1,2-g]-1,2-dihydroquinoline nucleus. The numbering of these condensed tricyclic systems is shown in the specification of U.S. Pat. No. 5,768,646 which is expressly incorporated herein by reference.

In a subsequent step of the inventive process, either the $X_1$ halogen substituent of the 7-halogeno-benzo[1,2-g]-chrom-3-ene, benzo[1,2-g]-thiochrom-3-ene or benzo[1,2-g]-1,2-dihydroquinoline derivative of Formula 3 or the halogen substituent $X_3$ of the reagent $X_3$—Y($R_2$)—A—B ($X_3$ is halogen, and the symbols Y, $R_2$, A and B are defined as in connection with Formula 1) is converted to a metal, so that one of these two compounds becomes an organometal reagent. These two compounds, that is the organometal reagent derived either from the compound of Formula 3 or from the compound $X_3$—Y($R_2$)—A—B and the other halogen substituted derivative are reacted, typically in the presence of a catalyst, to provide compounds of Formula 1 where the Y group is phenyl, naphthyl or heteroaryl. Typically the metal is zinc or lithium and the catalyst is a palladium complex, such as tetrakis-palladium(0) triphenylphosphine To obtain compounds of Formula 1 where Y is —$(CR_3=CR_3)_2$—, the compond of Formula 3 is reacted with a butadiene derivative of the formula $CHR_3=CR_3$—$CR_3=CR_3$—B where the symbols $R_3$ and B are defined as in connection with Formula 1. The latter reaction is conducted under conditions of a Heck reaction, typically in the presence of palladium(2) acetate and triphenylphosphine.

DETAILED DESCRIPTION OF THE INVENTION

The compounds made in accordance with the novel synthetic process of the present invention are used as agents that bind to retinoid receptors, and act as retinoids, retinoid antagonists and or retinoid inverse agonists. The manner of using the compounds made by the process of the present invention is described in U.S. Pat. No. 5,728,846.

Reaction Scheme 1 that is described above in connection with the Summary of the Invention discloses the two most important steps utilized in the synthetic process for making the compounds defined by Formula 1. Reaction Scheme 2 discloses the synthetic route in more detail.

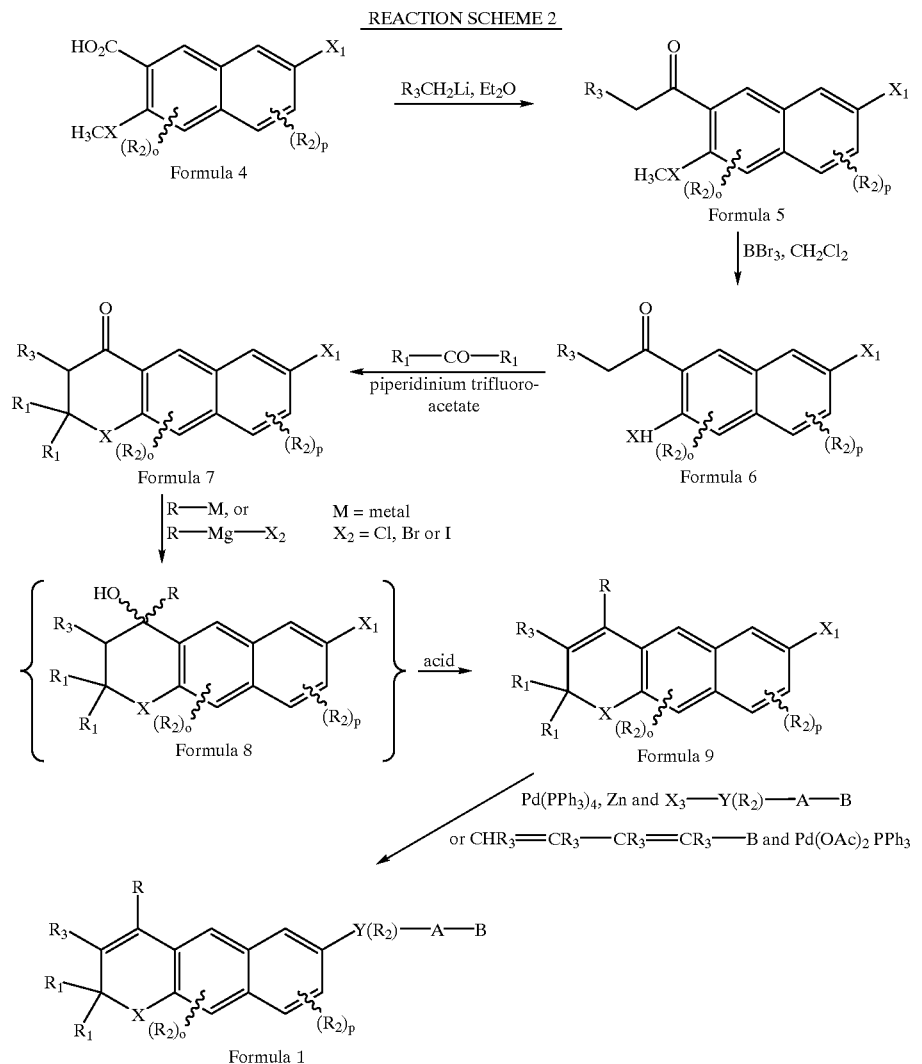

REACTION SCHEME 2

The starting compound in Reaction Scheme 2 is a 7-halogeno-2-naphthoic acid derivative ($X_1$ is Cl, Br or I) which is available in accordance with the chemical literature and wherein the symbols X, and $R_2$ are defined as in connection with Formula 1. An example for the starting compound of Formula 4 is 7-bromo-3-methoxy-2-naphthoic acid that is available in accordance with the publication Murphy, R. A. et al, J. Med. Chem. 1990 33, 171. Other examples are 7-bromo-3-methylthio-2-naphthoic acid and 7-bromo-3-methylamino-2-naphthoic acid. It will be recognized by those skilled in the art that instead of the 7-bromo derivative, the corresponding chloro or iodo derivative could also be used, however the bromo derivative is preferred and for this reason further reference will be made to the bromo compound. The compound of Formula 4 is converted to the corresponding ketone of Formula 5 for example by treatment with an organolithium reagent of the formula $R_3CH_2Li$ where $R_3$ is defined as in connection with Formula 1. In the presently preferred synthetic processes of the invention the reagent is methyl lithium ($R_3$ is H) and the resulting compound of Formula 5 is a 2-acetonaphtone derivative. The reaction with methyl (or other alkyl) lithium is conducted first at cold (−78° C.) temperature and thereafter the reaction mixture is allowed to warm to room temperature.

In the next step shown in Reaction Scheme 2, the $CH_3X$ function, such as the $CH_3O$ function is demethylated. This can be accomplished as indicated in the scheme by treatment of the compound of Formula 5 with boron tribromide to provide a 3-hydroxy, 3-mercapto or 3-amino-7-bromo-2-acetonaphthone derivative of Formula 6. Other reagents capable of bringing about the demethylation are HBr and boron trifluoride ethereate. The demethylation reaction with boron tribomide is also typically conducted at cold (−78° C.) temperature in methylene chloride or like aprotic solvent. The 3-hydroxy, 3-mercapto or 3-amino-7-bromo-2-acetonaphthone derivative of Formula 6 is thereafter condensed with a ketone of the formula $R_1$—CO—$R_1$ in the presence of piperidinium trifloroacetate (or like Lewis acid). The condensation reaction results in ring closure and the formation of 7-bromo-benzo[1,2-g]-chroman -4-one, 7-bromo-benzo[1,2-g]-thiochroman -4-one or 7-bromo-benzo[1,2-g]-1,2-tetrahydroquinolin -4-one derivative of Formula 7. The $R_1$ substituents are introduced into the 2-position of the condensed tricyclic ring system in the condensation reaction which is typically conducted in the presence of an excess of the ketone $R_1$—CO—$R_1$ by heating in an inert solvent (such as benzene) in a Dean-Stark apparatus by which water of the condensation is efficiently removed. Examples for the ketone of the formula $R_1$—CO—$R_1$ are acetone, methylethylketone and 3-pentanone, with acetone being preferred.

In the subsequent step shown in Reaction Scheme 2 the 7-bromo-2,2-dialkylbenzo[1,2-g]-chroman-4-one, 7-bromo-2,2-dialkylbenzo[1,2-g]-thiochroman-4-one or 7-bromo-2,2-dialkylbenzo[1,2-g]-1,2-tetrahydroquinolin-4-one derivative of Formula 7 is reacted with an organometallic reagent of the formula R—M or R—Mg—$X_2$ where M represents a metal, such as lithium or zinc, $X_2$ represents a halogen, such as bromine, and R is defined as in connection with Formula 1. Those skilled in the art recognize R—Mg—$X_2$ as a Grignard reagent derived from the compound R—$X_2$ and R—M as an organometal derivative, typically an organolithium derivative, that can be obtained from a reagent of the formula R—$X_2$ (preferably from R—Br) by treatment with an alkyl lithium, such as t-butyl lithium. It is an important aspect of the present invention that the reagent R—M or R—Mg—$X_2$ and the conditions of the reaction with the 7-bromo-2,2-dialkylbenzo[1,2-g]-chroman-4-one, 7-bromo-2,2-dialkylbenzo[1,2-g]-thiochroman-4-one or 7-bromo-2,2-dialkylbenzo[1,2-g]-1,2-tetrahydroquinolin-4-one derivative of Formula 7 are selected such, that the 7-halogeno, preferably 7-bromo function is left substantially intact in the reaction, and that the R group becomes covalently attached at the 4 position of the condensed tricyclic ring while the 4-one function is converted into a tertiary alcohol of Formula 8. Typically, the reaction of the compounds of Formula 7 with the reagent of R-lithium is conducted in an ether type solvent, such as tetrahydrofuran, in the cold, that is typically between −78° C. and 0° C. When R is an aryl, such as phenyl or substituted phenyl group the phenyl-lithium or substituted phenyl lithium reagent provides the desired selectivity, and the phenyl-lithium or substituted phenyl-lithium reagent is typically prepared in situ by treatment of the aryl halide with t-butyl lithium. When the R group is alkyl, then typically the corresponding Grignard reagent (alkyl—Mg—Br) is used, as the alkyl lithium reagent would not provide the desired selectivity. Presently the use of an aryl lithium reagent, particularly a phenyl or substituted phenyl lithium reagent is preferred. The tertiary alcohol compound of Formula 8 typically is not isolated from the reaction mixture, rather it is dehydrated to provide the corresponding 7-bromo-4-alkyl or aryl 2,2-dialkylbenzo[1,2-g]-chrom-3-ene, benzo[1,2-g]-thiochrom-3-ene or benzo[1,2-g]-1,2-dihydroquinoline compound of Formula 9.

In the next step of the reaction sequence the 7-bromo (or in the alternative the 7-iodo) substituent of the compounds of Formula 9 is converted to an organometal derivative and is reacted with a reagent of the formula $X_3$—Y($R_2$)—A—B where $X_3$ is halogen, preferably bromine or iodine) and the remaining symbols are defined as in connection with Formula 1. In other words, the reagent $X_3$—Y($R_2$)—A—B is a halogen substituted aryl or heteroaryl compound, preferably an ester of a halogen substituted aryl or heteroaryl carboxylic acid. Examples for the reagents of formula $X_3$—Y($R_2$)—A—B are ethyl 4-bromobenzoate, ethyl 2-bromopyridine-5-carboxylate, ethyl 2-bromopyridine-6-carboxylate, ethyl 2-bromothiophene-4-carboxylate, ethyl 2-bromothiophene-5-carboxylate, ethyl 2-bromofuran-4-carboxylate, and ethyl 2-bromofuran-5-carboxylate. These reagents are available in accordance with the chemical literature. The organometal derivative of the 7-bromo-4-alkyl or aryl 2,2-dialkylbenzo [1,2-g]-chrom-3-ene, benzo[1,2-g]-thiochrom-3-ene or benzo[1,2-g]-1,2-dihydroquinoline compound of Formula 9 can be a copper (Cu), lithium (Li), zinc (Zn) boron (B) or Grignard (Mg) derivative that is made in situ in accordance with the state of the art of preparing organometal reagents. The reaction between the halogen substituted aryl or heteroaryl compound of the formula $X_3$—Y($R_2$)—A—B and the compound of Formula 9 is typically conducted in an ether type solvent such as tetrahydrofuran (THF) in the presence of zinc and tetrakis-palladium(0) triphenylphosphine catalyst. Alternatively the compound of formula $X_3$—Y($R_2$)—A—B is converted into an organometal derivative (such as an organo-lithium, organo-zinc compound or a Grignard reagent) and is reacted with the halogen derivative of Formula 9. This type of reaction is illustrated below in the example disclosed in connection with Reaction Scheme 3.

In order to obtain compounds of Formula 1 where the Y group represents —($CR_3$=$CR_3$)$_2$—, the compound of Formula 9 is reacted with a butadiene derivative of the formula $CHR_3$=$CR_3$—$CR_3$=$CR_3$—B where $R_3$ and B are defined as in connection with Formula 1. The reaction with the butadiene derivative is conducted under the conditions of a Heck reaction, preferably in the presence of palladium(2) acetate and triphenylphosphine. The Heck reaction is described in detail in the treatise Heck, Richard F. "Palladium Reagents in Organic Synthesis" Academic Press (Orlando Florida) 1985, pp 374–381, incorporated herein by reference. An example for a preferred reagent used in the process of the present invention to prepare compounds of Formula 1 where the Y group represents —($CR_3$=$CR_3$)$_2$— is the pentadienoic acid ethyl ester of the formula $CH_2$=CH—C($CH_3$)=CH—$CO_2$Et which is available in accordance with the chemical literature Sundberg et al. J. Org. Chem. (1967) 32 p2938, expressly incorporated herein by reference.

The compounds of Formula 1 which are obtained in the above-described reactions can be subjected to transformations, such as saponification, transesterication, homologation, reduction of a carboxylic acid or ester function to the aldehyde or alcohol stage, and like reactions, in accordance with the state-of-the-art. These transformations are described in more detail in U.S. Pat. No. 5,728,846, (see Columns 12 and 13 of this reference patent).

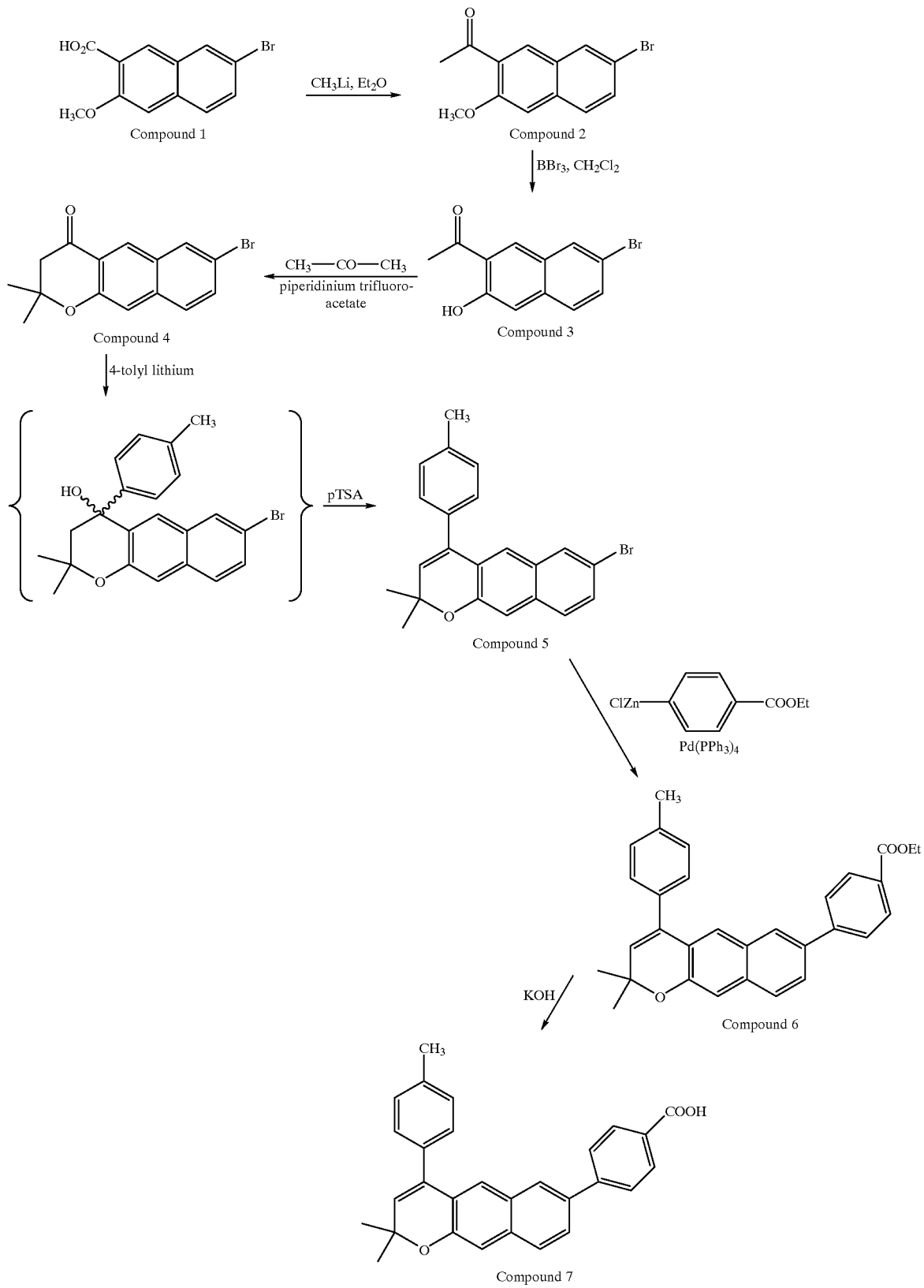
REACTION SCHEME 3

Reaction Scheme 3 discloses the preferred embodiment of the process of the present invention in which 4-[2,2-dimethyl-4-(tol-4-yl)-6,7-benzo[1,2-g]chrom-3-en-7-yl]benzoic acid (Compound 7) is prepared. 4-[2,2-Dimethyl-4-(tol-4-yl)-6,7-benzo[1,2-g]chrom-3-en-7-yl]benzoic acid (Compound 7) is described in U.S. Pat. No. 5,728,846 and is considered an important retinoic acid antagonist or inverse agonist compound. The following experimental section discloses in detail the reagents and conditions utilized in the preferred embodiment of the inventive process, as shown in Reaction Scheme 3.

SPECIFIC EXAMPLES

7-Bromo-3-methoxy-2-naphthoic acid (Compound 1)

7-Bromo-3-methoxy-2-naphthoic acid is obtained in accordance with the literature procedure of Murphy et al, J. Med. Chem. 1990 33, 171.

7-Bromo-3-methoxy-2-acetonaphthone (Compound 2)

To a cold (−78° C.) solution of 7-bromo-3-methoxy-2-naphthoic acid (Compound 1, 2.1 g, 7.5 mmol) in THF (20 mL) was added MeLi in ether (1.4 M solution, 11 mL, 15.4 mmol). The cooling bath was removed and the reaction mixture was warmed to room temperature over 20 minutes. The reaction was quenched by adding water (2 mL), and the resulting white precipitate was removed by filtration. The filtrate was concentrated to give the title compound as a pale yellow solid.

$^1$HNMR (CDCl$_3$): δ 2.68 (s, 3H), 4.01 (s, 3H), 7.16 (s, 1H), 7.57 (dd, J=1.9, 8.8 Hz, 1H), 7.62 (d, J=8.8 Hz, 1H), 7.99 (d, J=1.9 Hz, 1H), 8.06 (s, 1H).

7-Bromo-3-hydroxy-2-acetonaphthone (Compound 3)

To cold (−78° C.) solution of 7-bromo-3-methoxy-2-acetonaphthone (Compound 2, 950 mg, 3.4 mmol) in CH$_2$Cl$_2$ (10 mL) was added BBr$_3$ in CH$_2$Cl$_2$ (2 M solution, 2 ml, 4 mmol). The mixture was stirred for 15 minutes and then quenched by adding MeOH (1 mL), aqueous NaHCO$_3$ (5 mL), diluted with ether and EtOAc (60 mL). The organic layer was washed with brine, dried and solvent removed to obtain the title compound as a yellow solid.

$^1$HNMR (CDCl$_3$): δ 2.80 (s, 3H), 7.27 (s, 1H), 7.57 (s, 2H), 7.99 (s, 1H), 8.27 (s, 1H).

7-Bromo-2,2-dimethyl-6,7-benzo[1,2-g]chroman-4-one (Compound 4)

To a solution of piperidine (5 g, 58.8 mmol) in benzene (300 mL) was added trifluoroacetic acid (300 mg, 2.6 mmol) in benzene (5 mL) at room temperature. To this solution acetone (80 mL) was added followed by 7-bromo-3-hydroxy-2-acetonaphthone (Compound 3, 15 g, 56.8 mmol) in benzene (50 mL). The mixture was heated under a Dean-Stark apparatus for 5 days. Then the reaction mixture was washed with 10% HCl, 10% NaHCO$_3$, brine, dried and the solvent was removed by evaporation. The title compound was isolated as a yellow solid by silica gel flash chromatography.

$^1$HNMR (CDCl$_3$): δ 1.50 (s, 6H), 2.84 (s, 2H), 7.27 (s, 1H), 7.50–7.59 (m, 2H), 8.00 (s, 1H), 8.36 (s, 1H).

7-Bromo-2,2-dimethyl-4-(tol-4-yl)-6,7-benzol[1,2-g]chrom-3-ene (Compound 5)

To a cold (−78° C.) solution of 4-bromotoluene (5.7 g, 33.5 mmol) in THF (50 mL) was added t-BuLi (1.7M solution, 12.5 mL). The mixture was gradually warmed to approximately −10° C. over 30 minutes. Then the reaction mixture was cooled back to −78° C. and 7-bromo-2,2-dimethyl-6,7-benzo[1,2-g]chroman-4-one (Compound 4, 2.8 g, 9.2 mmol) in THF was added. The reaction mixture was then stirred at 0° C. for 2 hours. To the reaction mixture was added water (15 mL), diluted with EtOAc (250 mL), and was washed with brine, dried and the solvent was removed by evaporation. To the crude product CH$_2$Cl$_2$ (40 mL) and para-toluene sulfonic acid (pTSA, 40 mg) were added and the mixture was stirred at room temperature for 16 hours. The mixture was washed with 10% NaHCO$_3$ (10 mL), brine, dried and the solvent was removed by evaporation. Purification by flash chromatography on silica gel gave the title compound.

$^1$HNMR (CDCl$_3$): δ 1.54 (s, 6H), 2.45 (s, 3H), 5.85 (s, 1H), 7.21 (s, 1H), 7.27 (d, J=7.0 Hz, 4H), 7.35 (s, 1H), 7.42 (dd, J=1.9, 8.8 Hz, 1H), 7.53 (d, J=8.8 Hz, 1H), 7.76 (d, J=1.9 Hz, 1H).

Ethyl 4-[2,2-dimethyl-4-(tol-4-yl)-6,7-benzo[1,2-g]chrom-3-en-7-yl]benzoate (Compound 6)

To a mixture of 7-bromo-2,2-dimethyl-4-(tol-4-yl)-6,7-benzo[1,2-g]chrom-3-ene (Compound 5, 1 g, 2.6 mmol), with Pd(PPh$_3$)$_4$ (65 mg), was added THF (20 mL) followed by ethyl-4-(zinc chloro)benzoate (available from Rieke Metals Inc., 0.5 M solution in THF, 9 mL). The mixture was heated to 50° C. for 45 minutes, and thereafter another portion of ethyl-4-(zinc chloro)benzoate (0.5 M solution in THF, 9 mL) was added and heated to 50° C. for an additional 45 minutes. The reaction mixture was cooled to room temperature, quenched by adding aqueous NH$_4$Cl, diluted with EtOAc (150 mL) washed with brine, dried and the solvent was removed by evaporation. The title compound was isolated by flash chromatography on silica gel as a white solid.

$^1$HNMR (CDCl$_3$): δ 1.42 (t, J=7.1 Hz, 3H), 1.55 (s, 6H), 2.45 (s, 3H), 5.85 (s, 1H), 7.27 (d, J=7.0 Hz, 4H), 7.33 (d, J=8.5 Hz, 2H), 7.53 (s, 1H), 7.67 (dd, J=1.9, 8.6 Hz, 1H), 7.72–7.80 (m, 2H), 7.88 (s, 1H), 8.10 (d, J=8.5 Hz, 2H).

4-[2,2-Dimethyl-4-(tol-4-yl)-6,7-benzo[1,2-g]chrom-3-en-7-yl]benzoic acid (Compound 7)

A mixture of ethyl 4-[2,2-dimethyl-4-(tol-4-yl)-6,7-benzo[1,2-g]chrom-3-en-7-yl]benzoate (Compound 6, 470 mg, 1.1 mmol), THF (15 mL), MeOH (15 mL), KOH-H$_2$O (2M solution, 2 mL) was refluxed under argon for 2 hours. Then the solvent was removed by distillation, the residue diluted with H$_2$O (20 mL), extracted with ether (20 mL), the aqueous layer was acidified, and the product was isolated as a white solid by filtration from the aqueous layer.

$^1$HNMR (CDCl$_3$): δ 1.55 (s, 6H), 2.45 (s, 3H), 5.85 (s, 1H), 7.27 (d, J=7.0 Hz, 4H), 7.33 (d, J=8.5 Hz, 2H), 7.53 (s, 1H), 7.67 (dd, J=1.9, 8.6 Hz, 1H), 7.72–7.80 (m, 2H), 7.90 (s, 1H), 8.17 (d, J=8.5 Hz, 2H).

What is claimed is:

1. A process for preparing a compound of formula (1)

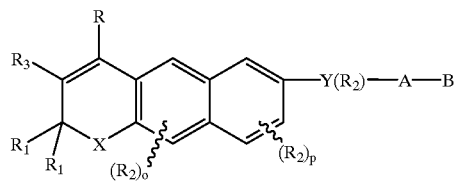

formula (1)

where X is O;

R is alkyl of 1 to 10 carbons, alkenyl of 1 to 10 carbons and of 1 to 3 double bonds, alkynyl of 1 to 10 carbons and of 1 to 3 triple bonds, aryl or (R$_4$)$_s$-heteroaryl where heteroaryl is selected from the group consisting of pyridyl, thienyl, furyl, pyridazinyl, pyrimidinyl, pyrazinyl, thiazolyl, oxazolyl, imidazolyl and pyrrazolyl;

R$_1$ is lower alkyl of 1 to 6 carbons;

$R_2$ and $R_4$ are alkyl of 1 to 6 carbons, F, Cl, Br, I, $NO_2$, $N_3$, $(CH_2)_p COOH$, $(CH_2)_p COOR_1$;

o, p and s are integers each independently having the value of 0 to 2;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or Y is $—(CR_3=CR_3)_2—$;

$R_3$ is H or lower alkyl of 1 to 6 carbons;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, with the proviso that when Y is $—(CR_3=CR_3)_2—$ then A is $(CH_2)_q$ and q is 0;

B is hydrogen, COOH or a pharmaceutically acceptable salt thereof, $COOR_8$, $CONR_9R_{10}$, $—CH_2OH$, $CH_2OR_{11}$, $CH_2OCOR_{11}$, CHO, $CH(OR_{12})_2$, $CHOR_{13}O$, $—COR_7$, $CR_7(OR_{12})_2$, $CR_7OR_{13}O$, or $Si(C_{1-6}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5-10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, the process comprising the steps of:

reacting a compound of formula (2)

formula (2)

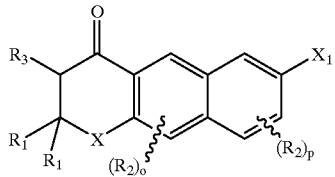

where $X_1$ is halogen with an organometal reagent of the formula R—M where M is a monovalent, divalent or trivalent metal, to selectively react with the endocyclic ketone function of the compound of formula (2) in preference over the halogen $X_1$, and to provide an intermediate tertiary alcohol;

dehydrating the intermediate tertiary alcohol to provide a compound of formula (3), and formula (3)

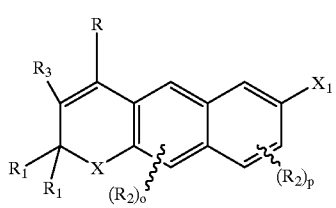

providing a reagent of the formula $X_3—Y(R_2)—A—B$ where $X_3$ is halogen, converting one of the compounds selected from the group consisting of the compound of formula (3) and a compound of the formula $X_3—Y(R_2)—A—B$ into an organometal reagent, and reacting the organometal reagent with the other compound of said group, or reacting the compound of formula (3) with a reagent of the formula $CHR_3=CR_3—CR_3=CR_3—B$ in the presence of a catalyst, to provide the compound of formula (1).

2. A process in accordance with claim 1 where X is O.

3. A process in accordance with claim 1 where the organometal reagent is $(R_4)_s$-phenyl-M.

4. A process in accordance with claim 3 where the organometal reagent is p-tolyl lithium.

5. A process in accordance with claim 1 where the reagent of the formula $X_3—Y(R_2)—A—B$ has the formula $X_3—C_6H_4—COOR_8$.

6. A process in accordance with claim 1 comprising the additional step of reacting a compound of formula (6)

formula (6)

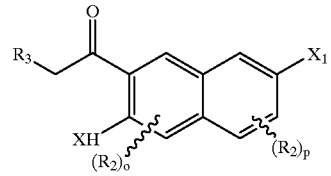

with a ketone of the formula $R_1—CO—R_1$ to provide the compound of formula (2).

7. A process in accordance with claim 6 wherein the step of reacting a compound of formula (6) with the ketone is performed in the presence of a Lewis acid catalyst.

8. A process in accordance with claim 6 comprising the additional step of demethylating a compound of formula (5)

formula (5)

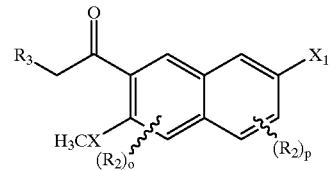

to provide the compound of formula (6).

9. A process in accordance with claim 8 wherein the step of demethylating is performed in the presence of a reagent selected from the group consisting of boron tribromide, hydrogen bromide and boron trifluoride ethereate.

10. A process in accordance with claim 8 comprising the additional step of reacting a compound of formula (4)

formula (4)

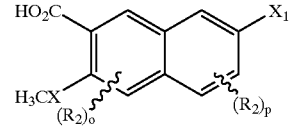

with an organometal reagent of the formula $R_3CH_2—M$, where M is monovalent, divalent or trivalent metal, to provide the compound of formula (5).

11. A process in accordance with claim 10 wherein the reagent of the formula (b)

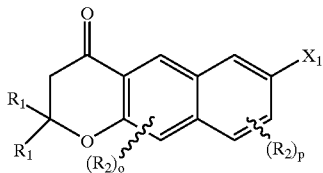

where $X_1$ is Cl, Br, or I, with a reagent of the formula $(R_4)_s$-phenyl-Li to provide an intermediate tertiary alcohol;

dehydrating said tertiary alcohol to provide a compound of formula (c)

formula (c)

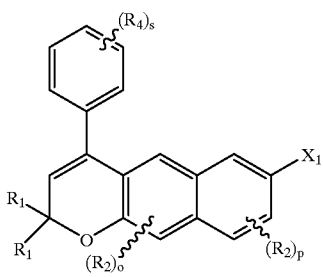

and converting one of said compounds selected from the group consisting of the compound of formula (c) and of formula (d) where $X_3$ is Cl, Br or I into an organometal reagent and reacting the organometal reagent with the other compound of said group to obtain the compound of formula (a).

formula (d)

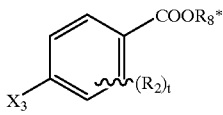

12. A process for pre paring a compound of formula (a)

formula (a)

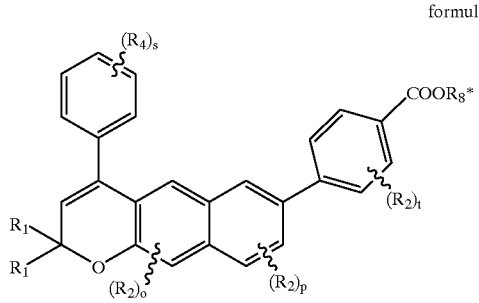

wherein $R_1$ is lower alkyl of 1 to 6 carbons;
$R_2$ and $R_4$ independently are alkyl of 1 to 6 carbons, F, Cl, Br, I, $NO_2$, $N_3$, $(CH_2)_p COOH$, $(CH_2)_p COOR_1$;
o, p, s and t each are integers, each independently having the value of 0 to 2;
and $R_8^*$ is H, or lower alkyl of 1 to 6 carbons, or a pharmaceutically acceptable salt of said compound, the process comprising the steps of reacting a compound of formula (b)

formula (b)

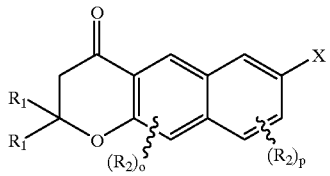

where $X_1$ is Cl, Br, or I, with a reagent of the formula $(R_4)_s$-phenyl-Li to provide an intermediate tertiary alcohol;

dehydrating said tertiary alcohol to provide a compound of formula (c)

formula (c)

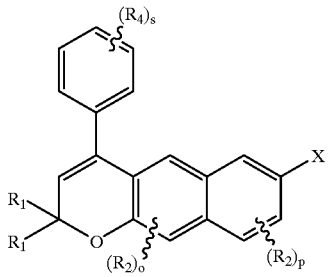

formula (d)

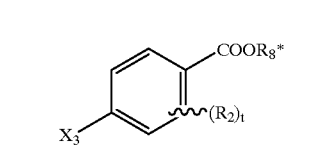

and converting one of said compounds selected from the group consisting of the compound of formula (c) and of formula (d) where $X_3$ is Cl, Br or I into an organometal reagent and reacting the organometal reagent with the other compound of said group to obtain the compound of formula (a).

formula (d)

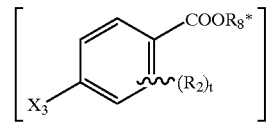

13. A process in accordance with claim 12 where the reagent $(R_4)_s$-phenyl-Li is 4-methylphenyl lithium.

14. A process in accordance with claim 12 where in the compound of formula (a) $R_1$ is methyl.

15. A process in accordance with claim 12 where in the compound of formula (a) o, p and t each are zero.

16. A process in accordance with claim 12 where in the compound of formula (a) $R_8^*$ is ethyl.

17. A process in accordance with claim 12 where the step of dehydrating is performed in the presence of acid.

18. The process of claim 12 that is used for the preparation of the compound of the formula

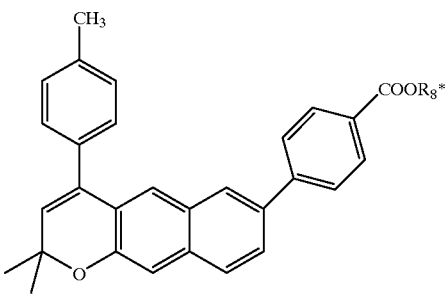

where $R_8^*$ is H or lower alkyl of 1 to 6 carbons.

19. A compound of the formula

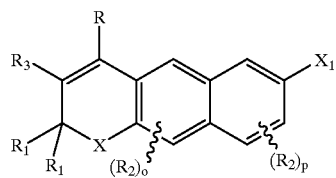

where X is O;

R is alkyl of 1 to 10 carbons, alkenyl of 1 to 10 carbons and of 1 to 3 double bonds, alkynyl of 1 to 10 carbons and of 1 to 3 triple bonds, aryl or $(R_4)_s$-heteroaryl where heteroaryl is selected from the group consisting of pyridyl, thienyl, furyl, pyridazinyl, pyrimidinyl, pyrazinyl, thiazolyl, oxazolyl, imidazolyl and pyrrazolyl;

$R_1$ is lower alkyl of 1 to 6 carbons;

$R_2$ and $R_4$ are alkyl of 1 to 6 carbons, F, Cl, Br, I, $NO_2$, $N_3$, $(CH_2)_p COOH$, $(CH_2)_p COOR_1$;

o, p and s are integers each independently having the value of 0 to 2;

$R_3$ is H or lower alkyl of 1 to 6 carbons, and $X_1$ is Cl, Br, or I, or a compound of said formula converted to an organometal reagent wherein the $X_1$ group has been exchanged with a metal selected from a group consisting of Cu, Li, Zn, B and Mg, said metal having any remaining valences attached to an anion.

20. A compound in accordance with claim 19 where $R_1$ is methyl.

21. A compound in accordance with claim 19 where R is $(R_4)_s$-phenyl.

22. A compound in accordance with claim 21 which is

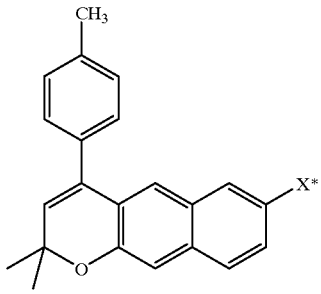

where X* is Br or a metal selected from the group consisting of Cu, Li, Zn, B and Mg said metal having any remaining valences attached to an anion.

* * * * *

UNITED STATES PATENT AND TRADEMARK OFFICE
CERTIFICATE OF CORRECTION

PATENT NO. : 6,043,381
DATED : March 28, 2000
INVENTOR(S) : Vuligonda et al.

It is certified that error appears in the above-identified patent and that said Letters Patent is hereby corrected as shown below:

Column 2,
Line 50, "$(CR_3=CR_3)_2$-" should be -- $-CR_3=CR_3)_2-$ --.

Column 6,
Line 66, "substituents ..." should not be a new paragraph.

Columns 14 & 15, claim 11,
Line 2, after "reagent of the", delete the rest of the claim and insert -- formula $R_3CH_2$-M is methyl lithium --.

Column 16,
Line 46, delete " 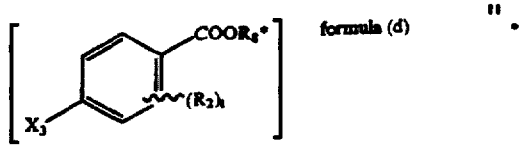 " .

Signed and Sealed this

Twenty-third Day of October, 2001

Attest:

NICHOLAS P. GODICI
Attesting Officer    Acting Director of the United States Patent and Trademark Office